(12) United States Patent
Friedrich et al.

(10) Patent No.: US 7,952,698 B2
(45) Date of Patent: May 31, 2011

(54) METHOD AND DEVICE FOR CONTACT ANGLE DETERMINATION FROM RADIUS OF CURVATURE OF DROP BY OPTICAL DISTANCE MEASUREMENT

(75) Inventors: Bernd Friedrich, Hasloh (DE); Jan-Gerd Frerichs, Norderstedt (DE); Eike Kortz, Bielefeld (DE)

(73) Assignee: Kruess GmbH Wissenschaftliche Laborgerate, Hamburg (DE)

( * ) Notice: Subject to any disclaimer, the term of this patent is extended or adjusted under 35 U.S.C. 154(b) by 333 days.

(21) Appl. No.: 12/349,925

(22) Filed: Jan. 7, 2009

(65) Prior Publication Data
US 2009/0180106 A1   Jul. 16, 2009

(30) Foreign Application Priority Data
Jan. 7, 2008 (DE) .......................... 10 2008 003 387

(51) Int. Cl.
*G01B 11/26* (2006.01)
(52) U.S. Cl. ........................ 356/138; 73/64.48; 73/64.52
(58) Field of Classification Search .................. 356/138; 73/64.52, 64.48, 53.01, 53.06, 61.48
See application file for complete search history.

(56) References Cited

U.S. PATENT DOCUMENTS

| 5,137,352 | A  | * | 8/1992 | Blitshteyn et al. | ............ 356/138 |
| 6,867,854 | B1 | * | 3/2005 | Wapner et al. | ................ 356/150 |
| 7,155,962 | B2 | * | 1/2007 | Knebel et al. | ................ 73/64.52 |

FOREIGN PATENT DOCUMENTS

WO   WO 03/073045    *  9/2003

\* cited by examiner

*Primary Examiner* — L. G Lauchman
(74) *Attorney, Agent, or Firm* — Staas & Halsey LLP

(57) ABSTRACT

A drop on a sample surface in a gaseous environment has a curved surface with a symmetry axis and a defined volume. To determine the contact angle, an object is imaged based on the reflection property of the surface of the drop, the position of the object with respect to the optical axis of an optical measuring system and the position of the object with respect to the sample surface, with the symmetry axis of the drop being arranged in or in the vicinity of the optical axis. The distance between the image and the optical axis of the drop is measured. The radius of curvature of the drop is determined based on the measured distance, and the contact angle is determined from the radius of curvature.

32 Claims, 2 Drawing Sheets

METHOD AND DEVICE FOR CONTACT
ANGLE DETERMINATION FROM RADIUS
OF CURVATURE OF DROP BY OPTICAL
DISTANCE MEASUREMENT

CROSS REFERENCE TO RELATED APPLICATIONS

This application is based on and hereby claims priority to German Application No. 10 2008 003 387.1 filed on Jan. 7, 2008, the contents of which are hereby incorporated by reference.

BACKGROUND

Described below are a method and a device for determining the contact angle between a sample surface, a gaseous environment and a drop arranged on the sample surface, the drop having a curved surface, a symmetry axis and a defined volume.

Here, the contact angle is the angle between the tangent to the contour of a drop and the straight line through the three-phase point of the drop on the sample surface, a drop of a known liquid being studied on a sample surface to be characterized. This angle is influenced inter alia by the surface tension of the drop, the surface energy of the sample surface being considered and the interfacial interaction between the drop and the sample surface. By determining the contact angle for drops of different liquids with known surface tensions, it is possible to deduce the surface energy of the sample.

There are various optical methods for contact angle determination. On the one hand, for example as in DE 197 54 765 C1 or KR 102 002 007 479 7 A, a shadow image method is employed in which the drop lying on a sample is observed laterally by a camera and the contact angle is determined with the aid of the two-dimensional recording of the drop contour and subsequent suitable image processing. The disadvantage of this drop-contour or shadow-image method is that the drop to be observed must be fully recorded by the camera.

On the other hand, the contact angle can be determined by a direct viewing method. Optics arranged above the sample, as well as a light source, are used here to record an image of the drop. The drop on a sample surface is illuminated with a direct light, so that the drop diameter can be determined by image analysis. With a known drop volume, the contact angle can be determined with the aid of the diameter of the drop.

To this end, it is known from JP 60 085 353 A to image a drop by a direct viewing method and, with the aid of the recording, to determine the diameter of the contact surface of the drop with the sample and the height of the drop. These two values are used to calculate the contact angle. WO 03/073045 A1 furthermore discloses a method in which a drop on a sample surface is recorded optically by a camera arranged above it. The bearing surface of the drop is subsequently calculated by a mathematical approximation of the drop surface to a circular surface.

Even in the contact angle determination methods carried out by the previously known direct viewing devices, it is necessary to image the drop fully so that the determination of a contact angle for a sample surface which has a very large area or is difficult to access, for example lying in a cavity, is not possible or is possible only with great outlay. The measurement of contact angles which are small, i.e. on drops which are significantly flattened, is also frequently not possible since these drops often cannot be recorded fully by the field of view of the camera optics owing to their large diameter.

A further disadvantage of the known methods with a direct viewing device is the generally low-contrast image relative to the sample surface, due to the transparency of the drop. This makes image analysis more difficult.

SUMMARY

An aspect is to provide a method and a device for contact angle measurement, which can be used independently of full imaging of the drop in the field of view of the recording optics being used. In this way, even drops which are not fully accessible can be used for the contact angle measurement. Another aspect is to provide a method and a device that constitute a more robust method and is richer in contrast, in order to permit more stable and more reliable image analysis.

First, an object may be imaged on the drop surface by using the reflection properties of the surface of a drop, the position of the object with respect to the optical axis of an optical measuring system and the position of the object with respect to the sample surface being known, and the symmetry axis of the drop being arranged in or in the vicinity of the optical axis. This imaging of an object on the drop surface is based on the assumption that the drop surface can be regarded as a convex (spherical) mirror.

A drop of liquid with both known surface properties and good reflection properties may be used, for example water, diiodomethane, ethanol, ethylene glycol. It is also possible to use other liquids.

The optical measuring system may be adapted to focus the image of the object and record it with optimal size. The optical measuring system includes suitable optics and a camera which is connected to an image analysis system, including image recognition and image processing, so that automated recording of the imaged object is possible. A digital or analogue video camera may be used. Other recording instruments, for example a still camera, may also be envisaged.

The positions of the optical measuring system and the objects to be imaged may be measured by one or a multiplicity of image sensors, so that a defined distance can be set and maintained or a distance which has been set can be determined accurately. This may for example be done by a simple mechanical spacer, although other sensors may also be envisaged, for example electrical (capacitive or inductive) or optical (laser or image) sensors which are electronically coupled to a suitable spacer.

In another embodiment, instead of an automatic electronic image analysis system, it is possible to use an eyepiece to recognize the images and to carry out the image recognition visually.

The optical axis of the optical measuring system may be arranged in the symmetry axis of the drop. Here, an approximate match of the two axes is sufficient. It is, however, also possible for the symmetry axis to extend at a distance from the optical axis.

If the drop lies on a horizontal flat surface, it can be arranged in a stationary fashion and the symmetry properties of the drop are not perturbed.

It is desirable for the volume of the drop to be as small as possible, for example no more than one microliter. It is however also possible to use a larger volume. A drop of at most one microliter is particularly well suited since it allows a relatively simple model of the drop to be assumed without having to take into account the effect of gravity on the drop, as is the case for larger volumes by the Gauss-Laplace equation.

Second, the distance between the image and the symmetry axis of the drop is measured. In an embodiment, the symmetry axis of the drop coincides with the optical axis of the optical measuring system, since in this case the distance of the image from the optical axis can be determined particularly simply by the known position of the object with respect to the sample surface and with respect to the optical axis.

This distance measurement may be carried out by an image analysis system, suitable image processing being used to determine the distance of the image from the optical axis.

In an embodiment, only that region of the drop in which the image and the symmetry axis of the drop lie is recorded by the optical measuring system in order to determine the distance of the image from the symmetry axis of the drop. This has the advantage that not necessarily the entire drop needs to lie in the field of view of the optical measuring system, so that the method is also suitable for drops in cavities, partially concealed drops or drops which are highly flattened. It is likewise possible to calculate the drop diameter and drop height from the measurement parameters.

Third, the radius of curvature of the drop is subsequently determined by the measured distance. On the basis of the known position of the object with respect to the optical axis of the optical measuring system, the known position of the object with respect to the sample surface and the known drop volume, it is in this case possible to correlate the measured distance with the radius of curvature of the supported drop. A more accurate description of use with two objects may be found below.

Based on the radius of curvature, the contact angle is determined. An explanatory description of this will likewise be given below.

In another embodiment, first a multiplicity of objects are imaged on the drop surface, the position of the objects with respect to one another and with respect to the sample surface being known. Next, is measurement of the distances of the images from one another or measurement of the distances of the images from the symmetry axis of the drop.

For example, the imaging can be of two objects on two images. In this case, the distance between the two images can be used as a measurement quantity for the radius of curvature. This has the advantage that the symmetry axis of the drop does not necessarily need to coincide with the optical axis of the camera. In this way, the arrangement of the measurement layout is simplified.

For carrying out multiple measurements to determine the contact angle by two images, it is helpful if the position of the drop with respect to the optical axis is reproducible. In another embodiment, the imaging can be of three objects on three images.

The measuring may include the placement of a circle through the images and determination of the radius of the circle as a measurement quantity for calculating the curvature of the surface of the drop. In this special embodiment, the method is independent of the symmetry axis of the drop so that it is not necessary to know the position of the objects to be imaged, with respect to the symmetry axis. First, the positions of the images with respect to one another are determined by the image analysis system. Subsequently, a circle is calculated which can be described uniquely by the positions of the three images. The radius of the calculated circle is subsequently determined as a measurement quantity for the drop curvature, from which the contact angle can be determined by the procedure described below.

The objects may be circularly arranged or circularly configured objects. The imaging of a circle onto a drop allows information about the symmetry properties of the drop to be obtained particularly well by any distortions occurring in the images of the objects.

In another procedure includes imaging a multiplicity of object pairs, each with a first object and a second object. The distances between the image of a first object and the image of a second object are subsequently determined for a multiplicity of object pairs, and an average value is formed from the radii of curvature respectively calculated.

Considered in terms of image analysis, the distance to be measured between the image of the first object and the image of the second object extends from a light intensity maximum of the image of the first object to a light intensity maximum of the image of the second object.

In another preferred embodiment, the distance between the images is established by determining a maximum of the light intensity using an image analysis method, for example surface centroid calculation. This method may, for example, be used when a unique intensity maximum cannot be found in the image of an object.

The method may further include calculation of the spread of the distances of the images of the objects from the symmetry axis of the drop. In this case, circularly arranged objects may be imaged by the reflection property of the drop surface. Particularly, the circularly arranged objects may be mirror-symmetrical with respect to the optical axis of the optical measuring system. A subsequent operation involves calculating the accuracy of the contact angle, which has been determined by the radius of curvature, which was in turn determined from the distances of the images from the symmetry axis of the drop.

Light sources may be used as objects which are imaged on the surface of the drop. The light sources may be light-emitting diodes, for example monochromatic light-emitting diodes or white light-emitting diodes. These have an advantage in that they have a small point-like luminous surface.

In another embodiment, it is also possible to use a light-emitting diode array as an object to be imaged. This may, for example, include different individually activatable light-emitting diodes, so that different object patterns can be generated by varying the switching states of the light-emitting diode matrix. Additional information about the drop geometry can be obtained in this way. Furthermore, by suitable selection of the individual activatable light-emitting diodes, a light-emitting diode array allows optimal illumination of the drop without the measurement layout having to be modified. Also, the objects to be imaged may be radiant light sources.

In another embodiment, with sufficient overall illumination of the drop surface, other objects may also be used, for example gratings.

The determination of the contact angle may be carried out by a geometrical-optics equation as a function of the distance of the image from the symmetry axis of the drop or the distances of two images from one another. In this case, it is assumed that light rays striking a liquid surface are reflected according to Snell's law. Since extremely small amounts of liquids are formed into drops with different curvature on a solid surface owing to the surface tensions, the drop surface is regarded as a convexly curved (spherical) mirror. In order to determine the sphere radius, the images of the objects are analyzed by suitable optics and image processing. With a constant drop volume, there is a direct relationship of the images and the contact angle $\phi$ of the drop with the sample surface.

For measuring the distance of an image from the optical axis, this method will be presented by way of example as follows:

$$\varphi = \cos^{-1}\left(-2\cos\left(\frac{1}{3}\left(\cos^{-1}\left(1 - \frac{3\left(1 + \frac{G}{B}\right)^3 V_7}{16\pi g^3}\right) + 4\pi\right)\right)\right).$$

Here, V, is the known drop volume, G is the known object height i.e. the distance of the optical axis from the object, g is the known distance of the object from the sample surface, the drop height being neglected here owing to the small drop size, and B is the image height i.e. the distance to be measured between the optical axis and the image.

Also, the determination of the contact angle is carried out by a correlation table. In this case, the contact angle of a drop on different sample surfaces is determined by any desired contact angle measuring layout. By applying the method to the same drop, the distances of images from one another and distances of the images from the optical axis on the same sample surfaces are also determined. These distances, which correlate with the drop's radius of curvature, may be a collated against the corresponding contact angles in a table. This table is in turn stored in the image analysis system.

In another embodiment of the method, the determination of the contact angle is carried out by regression analysis. In this case, the relationship between the radius of curvature of the drop and the contact angle is determined empirically for discrete support points, i.e. exemplary contact angle values, as in the correlation method described above. A suitable regression is subsequently carried out. The resulting function allows direct calculation of the contact angle from the distances measured by the method, and is stored in the image analysis system.

A device for measuring, based on image analysis, the contact angle between a horizontally aligned sample surface and a drop arranged on the sample surface in a gaseous environment includes a drop dosing device for applying a drop with a defined volume onto the sample surface, a light source, the position of which is known and which can be imaged on the drop surface, a camera having optics for recording the image of the light source on the drop, the position of the camera with respect to the sample surface being known, and an image analysis system which is connected to the camera, where the image analysis system is adapted to determine the distance of the image of the light source from the symmetry axis of the drop. The image analysis system includes image recognition and image processing, with which automated recording and evaluation of the images of the light source are possible.

Particularly, the symmetry axis of the drop lies on the optical axis of the camera optics. In this way, it is particularly easy to determine the distance of the image of the light source from the symmetry axis of the drop.

The camera is may be a digital or analog video camera, the optics of which are suitable for recording the images which are caused by the reflection properties of the surface of the drop. Other photodetecting sensors may also be envisaged instead of the camera.

In an embodiment, the light source is arranged circularly around the optical axis of the camera. In this case, for example, the light source may be aligned symmetrically with the optical axis.

In another embodiment, the contact angle measuring device includes multiple light sources. These may be separated both individually and circularly from the optical axis. The light sources may, for example, be arranged symmetrically with respect to the optical axis. Information about the symmetry properties of the drop can therefore be found.

The image analysis system may be suitable for determining the distances of the images from one another. An average value of the contact angles, determined from the distances of the images of the light sources from one another, may subsequently be calculated so as to increase the accuracy of the contact angle which is determined.

In an embodiment, the contact angle measuring device has two light sources. In this case, the distance between the two images can be used as a measurement quantity for the radius of curvature. When using only two light sources, whose distance from one another is known, the outlay for determining the distance between the two corresponding images is relatively small and the measurement can therefore be carried out rapidly.

In another embodiment, the image analysis device has three light sources which may be arranged circularly and symmetrically around the optical axis. In this embodiment, a circle is placed through the images and its coordinates are used to determine the radius of curvature. In this case, it is not necessary to know the positions of the images of the light sources with respect to the symmetry axis of the drop. The light sources may be diffusely radiating light sources.

In another embodiment, the light sources are configured in a point-like fashion so that only a small luminous surface is imaged. This facilitates identification of the images of the light sources and increases the accuracy of the contact angle to be determined. The image analysis device may include light-emitting diodes.

The light-emitting diodes may be monochromatic light-emitting diodes, white light-emitting diodes or a light-emitting diode array. The latter may for example include different individually activatable light-emitting diodes, so that different object patterns are generated by varying the switching states of the light-emitting diode matrix. Additional information about the drop geometry can be obtained in this way. Furthermore, by suitable selection of the individual activatable light-emitting diodes, a light-emitting diode array allows optimal illumination of the drop without the measurement layout having to be modified.

Furthermore in another embodiment, with sufficient overall illumination of the drop surface, other objects may also be used, for example gratings.

In an embodiment, the contact angle measuring device includes an automatic drop dosing device. Manual drop dosing devices may however also be used. Since the determination of the contact angle is based on the volume of the drop, it is necessary that the volume can be dosed reproducibly and in a defined way.

Also, the drop dosing device for applying the drop onto the sample surface may be arranged to apply the drop in a field of view of the camera. In this way, the drop can be applied in a controlled way onto the desired position on the sample surface. The images are not then recorded by the camera until the drop dosing device has been removed from the field of view of the camera. This may for example be made possible by suitable image processing software, a photoelectric barrier or a motion sensor.

In another embodiment, the light sources are arranged movably in a controlled way. The arrangement of the light sources can thereby be adapted individually to the corresponding sample and the drop placed on it.

The drop dosing device may include an adjustment system for the volume of the drop. Measurements of the contact angle can therefore be carried out with different volumes of the drop. Also, the drop dosing device may select the volume of the drop automatically so that a measurement series can be carried out automatically.

An embodiment of the device includes a camera, the optics of which automatically focus the drop placed on the sample surface. In this way, the distances of the image from the symmetry axis or of the images from one another can be measured rapidly and automatically.

Furthermore, in another embodiment, it is also possible to use the device at various positions on a sample, for example by a robot arm. In this case, automatic focusing represents a time saving compared to manual focusing.

In an embodiment, the contact angle measuring device is fastened to a stand by which the device can be positioned above a sample surface. Vibrations of individual components can thereby be prevented, and this also permits a contactless, automated measurement without the sample surface coming in contact with the measuring apparatus.

In an embodiment, a sensor measures the distance of the light sources from the surface of the drop. In this way, it is possible to determine the respective distance from the symmetry axis of the drop as well as the respective distances of various light sources from one another, and continuously to maintain a constant distance. The sensor may for example be a mechanical sensor, for example a spacer. Other sensors may however also be envisaged, for example electrical (capacitive or inductive) or optical (laser or image) sensors which are electronically coupled to a suitable spacer.

BRIEF DESCRIPTION OF THE DRAWINGS

These and other aspects and advantages will become more apparent and more readily appreciated from the following description of the exemplary embodiments, taken in conjunction with the accompanying drawings of which:

FIGS. 3 $b$) and 3 $c$) are schematic representations of three images of light sources on the surface of a drop.

DETAILED DESCRIPTION OF THE EXEMPLARY EMBODIMENTS

Figure 1:
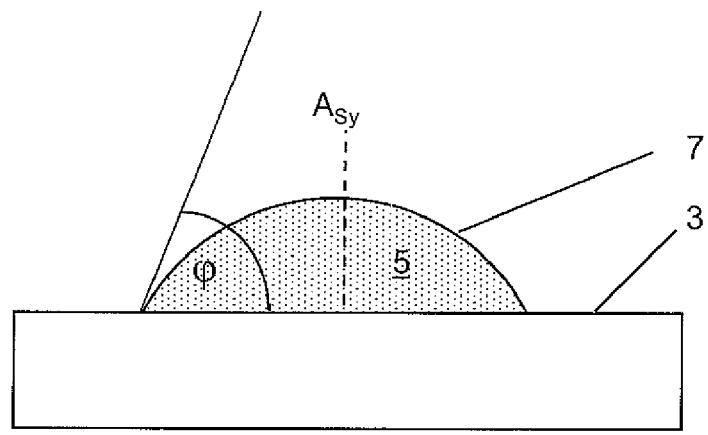
FIG. 1 is a cross sectional view illustrating a contact angle of a drop of a sample surface.

Reference will now be made in detail to exemplary embodiments, some of which are illustrated in the accompanying drawings, wherein like reference numerals refer to like elements throughout.

FIG. 1 shows a sample 1, on the surface 3 of which a drop 5 rests. Between the surface 3 of a sample 1, a gaseous environment and a drop 5, arranged on the surface 3 of the sample 1 and having a curved surface 7, a symmetry axis $A_{sy}$-$A_{sy}$ and a known constant volume $V_T$, there is the contact angle $\phi$.

The drop 5 may be a liquid with good reflection properties, for example a water drop.

The volume $V_T$ of the drop 5 may be no more than one microliter. Larger volumes may however also be envisaged. The order of magnitude of at most one microliter has the advantage that the effect of gravity on the drop can be neglected when calculating the radius of curvature of the drop 5.

The sample 1 may be a solid. It is however also possible, for example, for the sample 1 to be a gel with high viscosity. The sample 1 may be aligned horizontally with a flat surface. In one embodiment (not shown), the cavity 3 may also include cavities or be formed convexly or concavely, so long as the radius of curvature of the sample is sufficiently large compared with the drop diameter.

Figure 2:
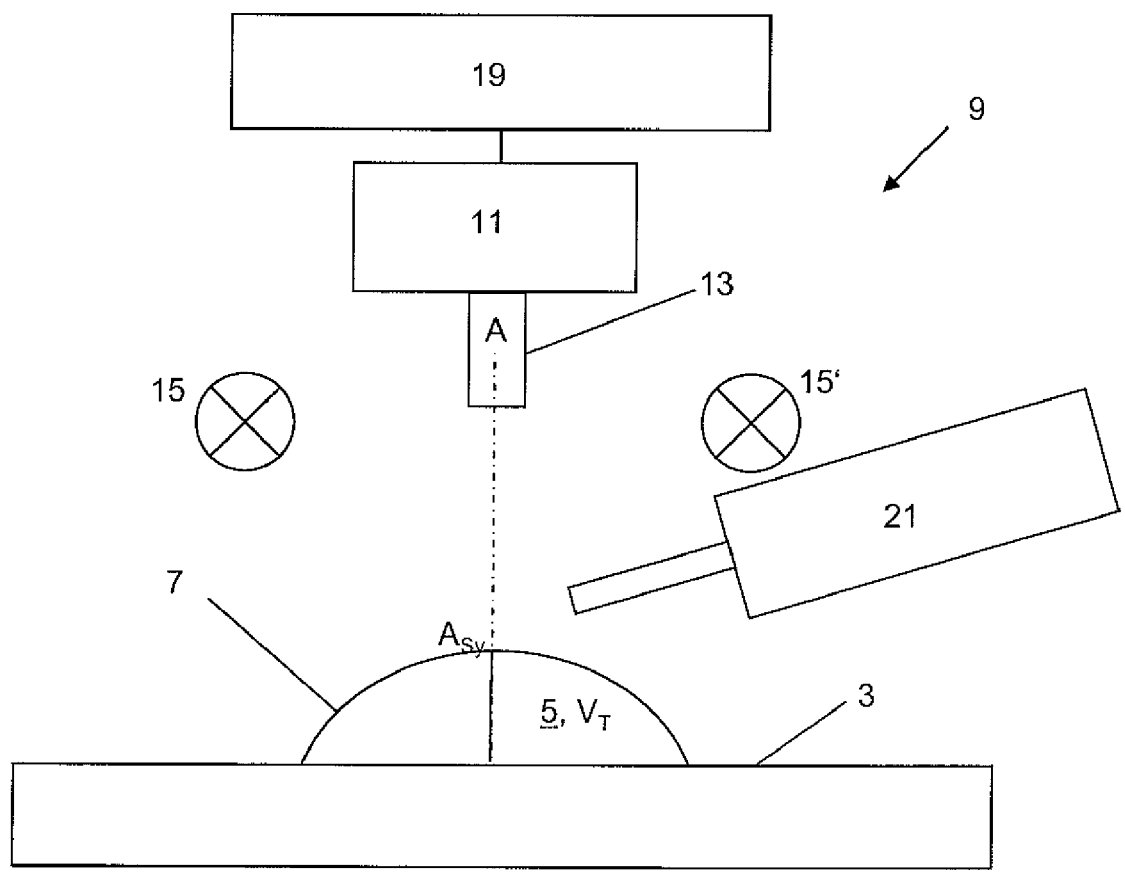
FIG. 2 is a block diagram of an image analysis device.

FIG. 2 represents a diagram of an image analysis device 9. On a horizontally aligned sample 1, there is a drop 5 which has a vertically aligned symmetry axis $A_{sy}$-$A_{sy}$. In another embodiment (not shown), the drop 5 is arranged in a cavity or lies on a convexly or concavely formed sample, so long as the radius of curvature of the sample is sufficiently large compared with the drop diameter.

In the illustrated embodiment, camera optics 11, the optical axis A-A of which extends congruently with the symmetry axis $A_{sy}$-$A_{sy}$ of the drop 5, is arranged above the drop 5. In this way, the outlay for determining the images is small.

In one embodiment (not shown), the optical axis A-A and the symmetry axis $A_{sy}$-$A_{sy}$ do not extend congruently.

The camera 11 may be a digital or analog video camera, the optics 13 of which are suitable for imaging the surface 7 of the drop 5. Other photodetecting sensors may however also be envisaged.

The embodiment of the image analysis device 9 as represented furthermore includes two light sources 15, 15', which are arranged symmetrically and at the same distance from the optical axis A-A of the camera 11 and from the symmetry axis $A_{sy}$-$A_{sy}$, the drop 5. The two light sources 15, 15' are imaged on the surface 7 of the drop 5. The positions of the light sources 15, 15' with respect to one another, or with respect to the $A_{sy}$-$A_{sy}$, are known. This makes it possible to calculate the distances of the light sources 15, 15', so that the object height G for calculating the contact angle $\phi$ is known.

In another embodiment (not shown), a multiplicity of light sources are used.

The light sources 15, 15', the positions of which are known, may in one embodiment (not shown) furthermore be arranged symmetrically around the optical axis A-A of the camera 11. In this way, information can be obtained about the symmetry properties of the drop 5.

In another embodiment, the light sources 15, 15', the positions of which are known, may be arranged asymmetrically with respect to the optical axis A-A so that a measurement can be carried out without accurate positioning of the light sources 15, 15'.

The light sources 15, 15' may be light-emitting diodes, for example monochromatic light-emitting diodes or white light-emitting diodes. These have the advantage that they have a small point-like luminous surface.

It is also possible to use a light-emitting diode array. This may for example include different individually activatable light-emitting diodes, so that different object patterns can be generated by varying the switching states of the light-emitting diode matrix. Additional information about the drop geometry can be obtained in this way. Furthermore, by suitable selection of the individual activatable light-emitting diodes, a light-emitting diode array allows optimal illumination of the drop 5 without the measurement layout having to be modified.

In another embodiment, diffusely radiating light sources 15, 15' may be used.

With sufficient illumination, which permits optical recording of the images 17, 17' of the light sources 15, 15' on the drop 5, gratings may also be used as light sources.

The camera 11 is connected to an image analysis system 19, which can record and evaluate the images 17,17' of the light sources 15,15'. In this case, it is not necessary for the camera 11 electrically connected to the image analysis system 19 to image the drop 5 fully. For calculating the distances of the images 17,17' of the light sources 15,15 from one another or from the symmetry axis $A_{sy}$-$A_{sy}$ of the drop 5, and for calculating the contact angle φ, it is sufficient for the images 17,17' and if appropriate also the symmetry axis $A_{sy}$-$A_{sy}$ of the drop 5 or the optical axis A-A of the camera 11 to lie in the field of view of the camera 11 and its optics 13. The camera 11 may include optics 13 which possess automatic focusing, so that the images of the light sources 15 on the surface 3 of the drop 5 can be recorded in a time-saving and simple fashion. It is, however, also possible to use a camera 11 with manual focusing.

In an embodiment (not shown), the image analysis device 9 includes distance sensors. These measure the distance of the camera 11 with a known path of its optical axis A-A from the light sources 15, the distance of the light sources 15 from one another and the distance of the light sources 15 from the surface 3 of the sample 5. In this way, the position of the image-generating and image-recording components of the measuring apparatus is known, so that the distance of the images 17 from one another or from the symmetry axis $A_{sy}$-$A_{sy}$ of the drop 5 can be measured or calculated by the image analysis system 19. The sensors may be mechanical sensors, for example spacers. It is however also possible to use electrical (capacitive or inductive) or optical (laser or image) sensors which are electronically coupled to a suitable spacer.

The embodiment furthermore may include a drop dosing device 21. This makes it possible to apply a drop 5 with a defined volume $V_I$ onto the surface 3 of the sample 5 in a reproducible way, e.g., using an automatic drop dosing device 21. It is however also possible to use a manual drop dosing device 21. To calculate the contact angle φ, it is necessary to be able to dose the volume $V_I$ of the drop 5 reproducibly.

In order to deposit the drop 5 onto the surface 3 of the sample 1, the drop dosing device 21 is brought into spatial proximity with the position on the surface 3 of the sample 1 which coincides with the optical axis A-A of the camera 11. The drop 5 can therefore be arranged at least partially in the field of view of the camera 11. The application of the drop 5 may be carried out manually or automatically.

In the illustrated embodiment, the drop 5 can be deposited in a controlled way by the drop dosing device 21 onto the desired position on the surface 3. In order to be able to record the images 17 of the light sources 15 by the camera 11 and the image analysis system 19, the drop dosing device 21 may be removed from the field of view of the camera 11 after the drop 5 has been applied. In one embodiment (not shown), this may for example be done using image processing software coupled to an automatic drop dosing device, a photoelectric barrier or a motion sensor. The drop dosing device 21 may include an adjustment system for the volume of the drop 5, so that the contact angle φ can be determined with different volumes $V_I$ of the drop 5. The drop dosing device 21 may select the volume $V_I$ of the drop 5 automatically so that a measurement series can be carried out in an automated fashion.

Figure 3:
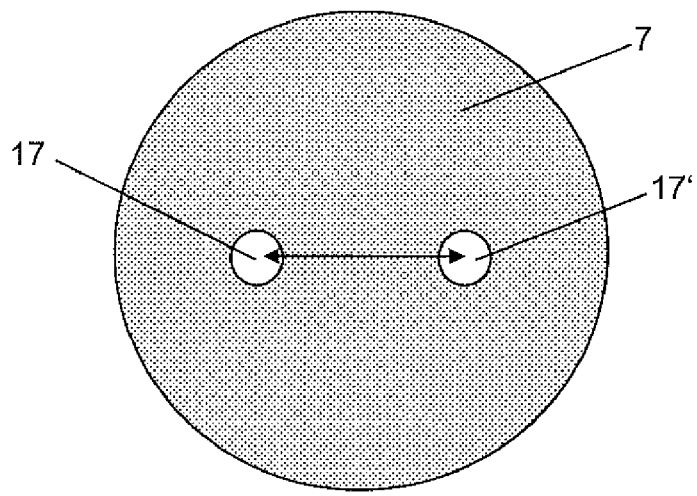
FIG. 3 $a$) is a schematic representation of two images of light sources on the surface of a drop.
Figure 3:
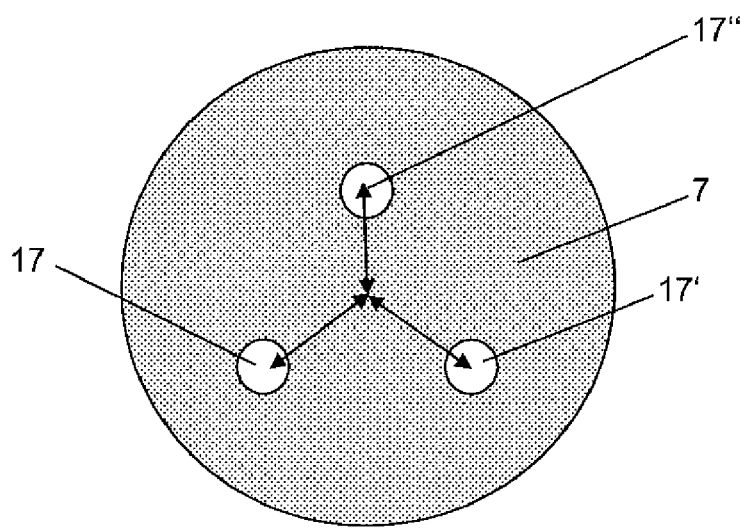
Figure 3:
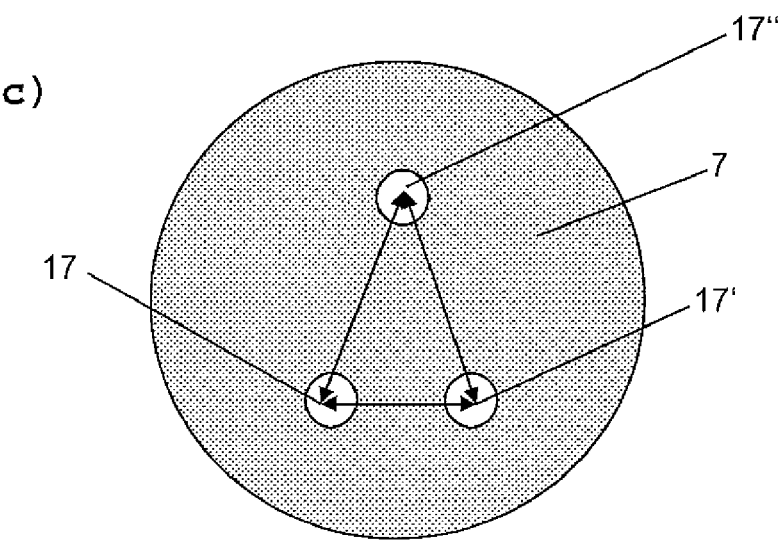

FIG. 3 a) shows two images 17, 17' of two light sources 15, 15' on a schematically represented surface 3 of a drop 5, which are arranged symmetrically with respect to the symmetry axis $A_{sy}$-$A_{sy}$ of the drop 5. The distance of the two images 17, 17' from one another, i.e. the image height B, is determined by the image analysis system 19. On the basis of the known position of the light sources 15, 15', it is furthermore possible to determine the distance of the light sources 15, 15' from one another, i.e. the object height G, and consequently the contact angle φ.

FIG. 3 b) shows the images 17, 17', 17" of three light sources 15, 15', 15". In order to determine the contact angle φ, the distances of the images 17, 17', 17" from the symmetry axis $A_{sy}$-$A_{sy}$ of the drop 5 are determined by the image analysis system 19. In this case, the symmetry axis $A_{sy}$-$A_{sy}$ of the drop 5 may coincide with the optical axis A-A for the camera 11.

The light sources 15 (not shown) may be arranged circularly in a plane arranged vertically with respect to the symmetry axis $A_{sy}$-$A_{sy}$ of the drop 5 and with respect to the A-A symmetry axis of the camera 11, and at an angle of 120° from one another. This allows uniform imaging of the light sources 15, 15', 15" on the surface 3 of the drop 5. From the measured distances, the measure of the radius of curvature can then be determined by forming the average value.

FIG. 3 c) shows an alternative procedure for determining the contact angle φ. In this case, it is not necessary for the optical axis A-A for the camera 11 and the symmetry axis $A_{sy}$-$A_{sy}$ of the drop 5 to extend congruently, since only the distances of the images 17, 17', 17" from one another are determined by the image analysis system 19. By using the images 17, 17', 17", it is possible to construct a unique circle whose radius represents a measure of the radius of curvature, from which the contact angle (p can then be determined.

From FIG. 3, the following relationship may be derived for the drop volume:

$$V_I = \int_{R-h}^{R} \pi \left( \sqrt{R^2 - x^2} \right)^2 dx \quad (1)$$

$$= \pi \int_{R-h}^{R} R^2 - x^2 \, dx$$

$$= \frac{1}{3} \pi h^2 (3R - h)$$

First, the unknown quantity h is calculated. The solution is found according to the Cardano method.

1. The general form:

$$0 = h^3 - 3Rh^2 + \frac{3}{\pi} V_I \quad (2)$$

$$Subst: h = y + R \quad (3)$$

$$-> 0 = (y + R)^3 - 3R(y + R)^2 + \frac{3}{\pi} V_I$$

$$\rightarrow 0 = y^3 - 3yR^2 - 2R^3 + \frac{3}{\pi} V_I \quad (4)$$

2. The discriminant T here reads:

$$T = \left(\frac{q}{2}\right)^2 + \left(\frac{p}{3}\right)^3 \text{ with } q = -2R^3 + \frac{3}{\pi} V_I; p = -3R^2 \quad (6)$$

$$T = \left(-R^3 + \frac{3}{2\pi} V_I\right)^2 + (-R^2)^3$$

$$= \frac{9}{4\pi^2} V_I^2 - \frac{3}{\pi} V_I R^3$$

$$T = V_I \left(\frac{9}{4\pi^2} V_I - \frac{3}{\pi} R^3\right)$$

In physically meaningful cases, we have:

$$V_T \leq \frac{4}{3}\pi R^3$$

from which it directly follows that:

$$T \leq V_T\left(\frac{9}{4\pi^2}\frac{4}{3}\pi R^3 - \frac{3}{\pi}R^3\right) = VR^3(0) = 0$$

Without restriction of application, the case $V_I = V_{sphere}$ may be neglected. The case thus existing here (T<0; "casus irreducibilis") thus makes it possible to solve the equation Eq. (4). There are three real solutions. The formulae for these read:

$$y_i = 2\sqrt[3]{\sqrt{-\left(\frac{p}{3}\right)^3}}\cos\left(\frac{\cos^{-1}\left(-\frac{q}{2\sqrt{-\left(\frac{p}{3}\right)^3}}\right)}{3} + \vartheta_i\right) \quad (7)$$

with $i \in \{1,2,3\}$; $\vartheta_i \in \{0°, 120°, 240°\}$ and p, q substituted as above $$y_i = 2\left(-\frac{p}{3}\right)^{\frac{1}{2}}\cos\left(\frac{\cos^{-1}\left(-\frac{q}{2}\left(-\frac{p}{3}\right)^{-\frac{3}{2}}\right)}{3} + \vartheta_i\right) \quad (8)$$

Substituting p and q back in:

$$y_i = 2\left(-\frac{(-3R^2)}{3}\right)^{\frac{1}{2}}\cos\left(\frac{\cos^{-1}\left(-\frac{\left(-2R^3+\frac{3}{\pi}V_I\right)}{2}\frac{1}{\left(\frac{(-3R^2)}{3}\right)^{\frac{3}{2}}}\right)}{3} + \vartheta_i\right) \quad (9)$$

$$= 2R\cos\left(\frac{\cos^{-1}\left(R^{-3}\left(R^3 - \frac{3}{2\pi}V_I\right)\right)}{3} + \vartheta_i\right)$$

$$= 2R\cos\left(\frac{\cos^{-1}\left(1 - \frac{3}{2\pi}\frac{V_I}{R^3}\right)}{3} + \vartheta_i\right)$$

Substituting h back in, Eq. (3) then leads to:

$$h_i = y_i + R \quad (10)$$

$$\Rightarrow h_i = 2R\cos\left(\frac{\cos^{-1}\left(1 - \frac{3}{2\pi}\frac{V_I}{R^3}\right)}{3} + \vartheta_i\right) + R$$

$$= R\left[2\cos\left(\frac{\cos^{-1}\left(1 - \frac{3}{2\pi}\frac{V_I}{R^3}\right)}{3} + \vartheta_i\right) + 1\right]$$

As can be shown experimentally, only the third solution formula with $\vartheta_3 = 240°$ gives meaningful results. Eq. (2) is therefore solved.

From FIG. 1, the following relationship may be derived between h and the contact angle CA=φ:

$$\cos(\varphi) = \left(\frac{R - h_i}{R}\right) \quad (11)$$

$$\Rightarrow CA = \varphi = \cos^{-1}\left(\frac{R - h_i}{R}\right)$$

The drop is regarded to a good approximation as a curved mirror. To satisfy this approximation well, liquids with a low refractive index are to be used.

The imaging equation for mirrors (in the near-axial range) from ray optics then applies:

$$\frac{1}{g} + \frac{1}{b} = \frac{1}{f} \quad (12)$$

with $f = \frac{R}{2}$ and $m = \frac{b}{g} = \frac{B}{G}$.

Substitution and rearrangement for R gives:

$$R = 2g\left(1 + \frac{G}{B}\right)^{-1} \quad (13)$$

$$\vartheta_3 = 240° = \frac{4}{3}\pi$$

If Eq. (10) with is substituted into Eq. (11), this gives $$CA = \varphi \quad (14)$$

$$= \cos^{-1}\left(\frac{R - h_i}{R}\right)$$

$$= \cos^{-1}\left(\frac{R - R\left[2\cos\left(\frac{\cos^{-1}\left(1 - \frac{3}{2\pi}\frac{V_I}{R^3}\right)}{3} + \frac{4}{3}\pi\right) + 1\right]}{R}\right)$$

$$= \cos^{-1}\left(1 - \left[2\cos\left(\frac{\cos^{-1}\left(1 - \frac{3}{2\pi}\frac{V_I}{R^3}\right)}{3} + \frac{4}{3}\pi\right) + 1\right]\right)$$

$$= \cos^{-1}\left(-2\cos\left(\frac{\cos^{-1}\left(1 - \frac{3}{2\pi}\frac{V_I}{R^3}\right)}{3} + \frac{4}{3}\pi\right)\right)$$

With Eq. (13), it then follows that:

$$CA = \varphi \quad (15)$$

$$= \cos^{-1}\left(-2\cos\left(\frac{\cos^{-1}\left(1 - \frac{3}{2\pi}\frac{V_I}{\left(2g\left(1+\frac{G}{B}\right)^{-1}\right)^3}\right)}{3} + \frac{4}{3}\pi\right)\right)$$

$$= \cos^{-1}\left(-2\cos\left(\frac{\cos^{-1}\left(1 - \frac{3\left(1+\frac{G}{B}\right)^3 V_I}{16\pi g^3}\right)}{3} + \frac{4}{3}\pi\right)\right)$$

Symbols and References Used
$V_I$ drop volume; $[V_I]=\mu l=mm^3$
R radius of the virtual sphere of which the real drop and represents a segment; [R]=mm
h height of the drop; [h]=mm
p, q auxiliary variables in calculations (defined and explained in the respective calculation)

f image focal length (here=object focal length); [f]=mm
g object distance (distance of light source–drop apex); [g]=mm
b image distance (distance of image–drop apex); [b]=mm
B image height (distance of optical axis–reflection); [B]=mm
G object height (distance of optical axis–light source); [G]=mm
CA contact angle; [CA]=°

The system also includes permanent or removable storage, such as magnetic and optical discs, RAM, ROM, etc. on which the process and data structures of the present invention can be stored and distributed. The processes can also be distributed via, for example, downloading over a network such as the Internet. The system can output the results to a display device, printer, readily accessible memory or another computer on a network.

A description has been provided with particular reference to exemplary embodiments thereof, but it will be understood that variations and modifications can be effected within the spirit and scope of the claims which may include the phrase "at least one of A, B and C" as an alternative expression that means one or more of A, B and C may be used, contrary to the holding in Superguide v. DIRECTV, 358 F3d 870, 69 USPQ2d 1865 (Fed. Cir. 2004).

What is claimed is:

1. A method for determining the contact angle between a sample surface, a gaseous environment and a drop arranged on the sample surface, the drop having a curved surface, a symmetry axis and a defined volume, comprising:
    imaging an object on the basis of the reflection properties of the surface of the drop, the position of the object with respect to the optical axis of an optical measuring system and the position of the object with respect to the sample surface being known, and the symmetry axis of the drop being arranged in or in the vicinity of the optical axis;
    measuring the distance between the image of the object and the symmetry axis of the drop;
    determining the radius of curvature of the drop from the measured distance; and
    determining the contact angle from the radius of curvature.

2. A method according to claim 1,
    wherein said imaging obtains images of multiple objects, the position of the objects with respect to one another, with respect to the optical axis and with respect to the sample surface being known, and
    wherein said measuring obtains the distances of the images of the objects from one another or measurement of the distances of the images from the symmetry axis of the drop.

3. A method according to claim 2, wherein said imaging obtains the images of two objects.

4. A method according to claim 2, wherein said imaging obtains the images of three objects.

5. A method according to claim 4, wherein said measuring comprises:
    placing a circle through the images of the objects; and
    determining the radius of the circle as a measure of the curvature of the surface of the drop.

6. A method according to claim 5, wherein said imaging obtains images of circularly arranged objects.

7. A method according to claim 6,
    wherein said imaging obtains the images of multiple object pairs, each with a first object and a second object, and
    wherein said measuring comprises determining the distances between the image of a first object and the image of a second object for a multiplicity of object pairs.

8. A method according to claim 7, further comprising:
    calculating the spread of the distances of the images of the objects from the symmetry axis of the drop to determine the symmetry of the drop; and
    calculating the accuracy of the contact angle determined by the radius of curvature.

9. A method according to claim 8, wherein the optical measuring system comprises a digital or analogue video camera.

10. A method according to claim 9, wherein the objects are light sources.

11. A method according to claim 10, wherein the light sources are light-emitting diodes.

12. A method according to one of claim 11, wherein the determination of the contact angle is carried out by a geometrical-optics equation as a function of the distance or distances determined by said measuring.

13. A method according to one of claim 11, wherein the determination of the contact angle is carried out by a correlation table.

14. A method according to one of claim 11, wherein the determination of the contact angle is carried out by regression analysis.

15. An image analysis device for measuring a contact angle between a sample surface, a gaseous environment and a drop arranged on the sample surface, comprising:
    the sample surface, having a first known position;
    a drop dosing device for applying the drop with a defined volume onto the sample surface, the drop having a surface and a symmetry axis;
    a light source, having a second known position, capable of directing an image on the surface of the drop;
    a camera having optics for recording the image of the light source on the drop and an optical axis with a third known position; and
    an image analysis system connected to the camera, the image analysis system adapted to determine a distance of the image of the light source from the symmetry axis of the drop.

16. An image analysis device according to claim 15, wherein the light source is arranged circularly around the optical axis of the camera.

17. An image analysis device according to claim 16, wherein the light source comprises a plurality of light sources producing images.

18. An image analysis device according to claim 17, wherein the image analysis system determines distances of the images of the light sources from one another.

19. An image analysis device according to claim 17, wherein the plurality of light sources are two light sources.

20. An image analysis device according to claim 17, wherein the plurality of light sources are three light sources.

21. An image analysis device according to claim 17, wherein the light sources are diffuse light sources.

22. An image analysis device according to claim 17, wherein the light sources are point light sources.

23. An image analysis device according to claim 22, wherein the point light sources are light-emitting diodes.

24. An image analysis device according to claim 23, wherein the light-emitting diodes are selected from monochromatic light-emitting diodes, white light-emitting diodes and a light-emitting diode array.

25. An image analysis device according to claim 17, wherein the light sources are arranged movably.

26. An image analysis device according to claim 17, further comprising a sensor measuring the distance of the light sources from the surface of the drop.

27. An image analysis device according to claim 26, wherein the sensor is one of an electrical, optical or mechanical sensor.

28. An image analysis device according to claim 15,
wherein the drop dosing device is arranged to apply the drop in a field of view of the camera, and
wherein the light source produces the image on the surface of the drop after the drop dosing device has been removed from the field of view of the camera.

29. An image analysis device according to claim 15, wherein the drop dosing device is an automatic drop dosing device.

30. An image analysis device according to claim 29, wherein the drop dosing device comprises an adjustment system for the defined volume of the drop.

31. An image analysis device according to claim 30, wherein the drop dosing device automatically selects the defined volume of the drop.

32. An image analysis device according to claim 15, wherein the optics of the camera focus the drop automatically.

* * * * *